United States Patent [19]

Yagi et al.

[11] 4,317,881

[45] Mar. 2, 1982

[54] PROCESS FOR PRODUCING CYCLODEXTRINS

[75] Inventors: Yoshiaki Yagi, Fujisawa; Kageaki Kouno, Tokyo; Taiji Inui, Chigasaki, all of Japan

[73] Assignee: Sanraku-Ocean Co., Ltd., Tokyo, Japan

[21] Appl. No.: 134,255

[22] Filed: Mar. 26, 1980

[30] Foreign Application Priority Data

Apr. 7, 1979 [JP] Japan ................................. 54/42290

[51] Int. Cl.$^3$ ......................... C12N 9/10; C12P 19/18
[52] U.S. Cl. ..................................... 435/97; 435/193; 435/859
[58] Field of Search ......................... 435/97, 859, 193

[56] References Cited

U.S. PATENT DOCUMENTS

| 3,652,398 | 3/1972 | Armbruster et al. | 435/97 |
| 3,812,011 | 5/1974 | Okada et al. | 435/97 |
| 3,923,598 | 12/1975 | Horikoshi | 435/97 |
| 3,988,206 | 10/1976 | Shiosaka | 435/97 X |
| 4,135,977 | 1/1979 | Horikoshi et al. | 435/97 |

*Primary Examiner*—Esther M. Kepplinger
*Attorney, Agent, or Firm*—Jordan and Hamburg

[57] ABSTRACT

A process for producing cyclodextrins which comprises using cultured medium of the strains belonging to genus Micrococcus, filtrate thereof or enzyme preparation obtained therefrom, especially, the process in which the ratio of α-cyclodextrin to β-cyclodextrin can be desirably varied by regulating the condition of the reaction mixture, is disclosed.

8 Claims, 6 Drawing Figures

PROCESS FOR PRODUCING CYCLODEXTRINS

BACKGROUND OF THE INVENTION

(1) Field of the Invention

The present invention relates to a process for producing cyclodextrins and, more particulary, to a process which comprises cultivating microorganisms belonging to genus Micrococcus capable of producing cyclodextrin glycosyltransferase (E.C. 2.4.1.19), treating starch or degraded starch with the enzyme obtained by said cultivation or a composition containing such enzme to provide cyclodextrins and, if desired, recovering cyclodextrins thus produced.

The cyclodextrins according to the present invention are crystalline dextrin, which are also called "Schardinger dextrin".

They are cyclic oligosaccharide composed of 6, 7 or 8 glucose residues which are bound by α-1,4-bonds. They are called α-, β- or γ-cyclodextrin depending on the number of carbon residue, 6, 7 or 8, respectively.

The cyclodextrin has been known as monomolecular host molecule which has torus in the molecule capable of including various kinds of organic compounds (guest compounds). This specific inclusion has been widely used in fields of medicine, agricultural chemicals, foods, cosmetics, perfumes and the like.

(2) Description of the Prior Art

The process for preparation of the cyclodextrins have already described by Tilden and Hudson (J. Am. Chem. Soc. 64, 1432 (1942) ) and D. French (J. Am. Chem. Soc. 71, 353 (1949) ), in which the cyclodextrins have been produced by treating starch with the enzyme from *Bacillus macerans*, the so-called "macerans amylase".

Recently *Bacillus stearothermophilus* (Proc. Symp. Amylases (Osaka) 18, 43 (1973) ) (Japan Kokai SHO 50-63189), *Bacillus megaterium* (Agr. Biol. Chem. 38, 387 (1974) ) (Japan Kokai SHO 48-40996), *Bacillus circulans* (Proc. Symp. Amylases (Osaka) 18, 21, (1973) ), *Bacillus ohbensis* sp. (Japan Patent Publication SHO 52-31949) and Bacillus sp. No. 38-2 (ATCC 21783) (Die Stärke, 27, 410 (1975) ) have been known as a microorganism which produces a similar enzyme. All the microorganisms belong to genus Bacillus. As such strain belonging to genus other than Bacillus, only *Klebsiella pneumoniae* M5 (Arch. Microbiol. 111, 271 (1977) ) has been reported. But there has been no report on production of such enzyme by any microorganism except for the microorganisms belonging to genus Bacillus and *Klebsiella pneumoniae* M5.

Characteristics of the Process of the Invention

It has been discovered by the present inventors that two strains newly isolated from soil and belonging to genus Micrococcus produce a similar enzyme to known one produced by the microorganisms belonging to genus Bacillus and Klebsiella.

It has been further discovered that the enzyme produced by the micrococci is highly thermostable in wide range of pH and has high producibility of the cyclodextrins.

It has been furthermore found that industrial production of the cyclodextrins can be advantageously accomplished by use of the enzyme.

Furthermore, the present invention provides a process for producing cyclodextrins, as one of the embodiments, in which α-cyclodextrin and β-cyclodextrin can be produced in desired ratio. Namely it has been reported that, in conventional processes, for example, cyclodextrin glycosyltransferases from *Bacillus macerans, Bacillus stearothermophilus* and *Klebsiella pneumoniae* M5 mainly provide α-cyclodextrin and those from *Bacillus megaterium, Bacillus circulans, Bacillus ohbensis* sp. and Bacillus sp. No. 38-2 give β-cyclodextrin as their main product.

On the other hand, although cyclodextrin glycosyltransferase according to the present invention usually produces β-cyclodextrin, appropriate regulation of pH and substrate and enzyme concentrations in the enzyme reaction mixture enables to raise a ratio of α-cyclodextrin to β-cyclodextrin in the reaction product.

OBJECTS OF THE INVENTION

Accordingly, it is an object of this invention to provide a new process for producing cyclodextrins from starch or degraded starch by using cultured medium of newly isolated strains belonging to genus Micrococcus, filtrate thereof or enzyme preparation obtained therefrom.

Another object of this invention is to provide an enzyme source of cyclodextrin glycosyltransferase which is high thermostable in wide range of pH and has highly producibility of the cyclodextrins.

Still another object of this invention is to provide a new process in which the ratio of α-cyclodextrin to β-cyclodextrin can be desirably regulated.

SUMMARY OF THE INVENTION

Therefore, the present invention provides a process for producing the cyclodextrins which comprises cultivating a microorganism belonging to genus Micrococcus capable of producing cyclodextrin glycosyltransferase in a nutrient medium and treating starch or degraded starch with a cultured medium obtained by said cultivation, medium filtrate, concentrate thereof or an enzyme preparation obtained from various steps of purification, to give cyclodextrins.

Furthermore, the present invention also provides a process for desirably regulating a ratio of α- and β-cyclodextrins in the enzyme reaction product.

DETAILED EXPALNATION OF THE INVENTION

The microorganism according to the present invention belongs to genus Micrococcus, which differs from the conventional bacilli known as cyclodextrin glycosyltransferase-producing strain. For this purpose, two strains which are highly capable of producing such enzyme and named M 849 and B 645, respectively, have been selected and taxonomically identified. These strains are deposited with Fermentation Research Institute, Agency of Industrial Science and Technology as the culture number FERM-P No. 4912 and FERM-P No. 4913, respectively.

The taxonomical study of the strains was performed according to a paper, "Methods for Classifying Staphylococci and Micrococci", presented by Baird Parker appeared in "Identification Methods for Microbiologist" I (Part A) (Ed. by B. M. Gibbs and F. A. Skinner, 1966) and papers described by the same author in J. Gen. Microbiol. 30, 409 (1963) and 38, 363 (1965). Reports by J. B. Evans and W. E. Kloos appeared in Appl. Microbiol. 23, 326 (1972), and M. Kocur and T. Martinec appeared in International Journal of Systematic Bacteriology 22, 218 and 228 (1972), and also Bergy's Manual of Determinative Bacteriology, 8th Ed. (1974) were also referred.

(1) Taxonomical characteristics of strain M 849 (FERM-P No. 4912) (ATCC 31606)

(a) Morphology (i) Vegetative cell: Spheres, 0.9–1.5 μm in diameter.

(ii) Occurring singly, in pairs or tetrads, sometimes in irregular clusters.

(iii) Non-motile.

(iv) Spores not formed.

(v) Gram-positive.

(b) Cultural characteristics (Cultivated at 30° C. for 2 days unless otherwise noted)

(i) Nutrient agar plate

Colonies were circular, white, smooth glistening, opaque and convex with a regular edge.

(ii) Nutrient agar slant

Good growth in filiform. White, opaque and glistening colonies with a smooth surface and regular edge. Sometimes wavy edge in old culture. Medium unchanged.

(iii) Nutrient broth

Turbid with viscous sediment. Pellicle and ring not formed. Odorless. Pigment not formed.

(iv) Nutrient gelatin stab (20° C.)

Slow and only surface growth at early stage. Very slight liquefaction after more than 15 days. Slight ability to liquefy gelatin was shown by other test.

(v) Litmus milk

Unchanged at early stage but acidic after 5–10 days. No coagulation, peptonization and decolorization of litmus were shown.

(c) Physiological characteristics (i) Reduction of nitrates: Positive.

(ii) Gas production in nitrate broth: Negative.

(iii) MR test: Slightly positive.

(iv) Acetoin production: Negative.

(v) Indole production: Negative.

(vi) $H_2S$ production: Negative.

(vii) Starch hydrolysis (in nutrient medium supplemented with 0.2–1.0% soluble starch): Negative at pH 7.0 and Positive at pH 9.5.

(viii) Citrates utilization: Negative in Christensen's and Simmons' media.

(ix) Pigment: Not produced.

(x) Urease: Positive.

(xi) Oxidase (Kovac's method): Negative.

(xii) Catalase: Positive in nutrient broth and nutrient agar supplemented with 1% glucose.

(xiii) Growth conditions: Optimum pH for growth was 6.8–8.5 and good growth even at pH 9.5. Almost no growth below pH 5.0. Optimum temperature was 27°–37° C. Growth occurred at 40° C. or 20° C. but scant growth at 10° C. No growth at 45° C.

(xiv) Behavior to oxygen: Aerobic.

(xv) OF test: Oxidative. Acid was produced oxidatively from glucose and mannitol but no gas produced. No gas and acid production under anaerobic condition.

(According to the method recommended by International Subcommittee on Staphylococci and Micrococci, Intern. Bull. Bact. Nomencl. Taxon. 15 109, 1965.)

(xvi) Acid production from various sugars under aerobic condition:

| | | |
|---|---|---|
| (1) | L-Arabinose | − |
| (2) | D-Xylose | − |
| (3) | D-Glucose | + |
| (4) | D-Mannose | + |
| (5) | D-Fluctose | + |
| (6) | D-Galactose | + |
| (7) | Maltose | + |
| (8) | Sucrose | + |
| (9) | Lactose | + |
| (10) | Trehalose | + |
| (11) | D-Sorbitol | − |
| (12) | D-Mannitol | + |
| (13) | Inositol | − |
| (14) | Glycerine | + |
| (15) | Starch | − |

+: Production
−: Not produced

No gas production from all the carbohydrates.

(xvii) Degradation of esculin: Negative (Slight degradation after a long-term culture).

(xviii) Degradation of hippuric acid: Positive.

(xix) Degradation of arginine: Negative.

(xx) Deamination of phenylalanine: Negative.

(xxi) Coagulase: Negative.

(xxii) Hemolysis: Negative.

(xxiii) Sodium chloride tolerance: Good growth in nutrient medium containing 15% and less NaCl. Slow and scant growth in 18% or 20% NaCl-containing medium.

(xxiv) Phosphatase: Negative.

(xxv) Degradation of Tween 80: Negative.

(xxvi) Growth on an inorganic nitrogen agar:

Almost no growth (according to Kloos' method. International J. System. Bacteriol. 24, 79, 1974).

(xxvii) Liquefaction of gelatin: Slight liquefaction (according to Frazier gelatin agar method).

(xxviii) Hydrolysis of casein: Negative (according to solubilization in skim milk agar).

(xxix) DNase: Negative.

It is evident from the above-mentioned results that the strain M 849 capable of producing the enzyme according to the present invention is assigned to a bacteria belonging to genus Micrococcus. There are described sixteen species of bacteria as micrococci in Bergey's Mannual of Determinative Bacteriology, 7th Edition (1957). Genus Sarcina is also described as an independent genus. The latest 8th edition of the same mannual contains only three species in genus Micrococcus, that is, *Micrococcus luteus*, *M. varians* and *M. roseus*, where genus Sarcina is eliminated and many species classified to genus Micrococcus before are reclassified to the three species based on further studies. *Micrococcus varians* may be selected as the most resembled species by comparing the taxonomical characteristics of strain M 849 with those of the said three described micrococcal species. According to the described characteristics of

*M. varians,* colonies on a nutrient agar or other common media are yellow. This is one of the most important characteristics to distinguish *M. varians* from *M. roseus.* However, in the above-referred Baird Parker's paper, the subgroup 5 of genus Micrococcus which he has proposed, contains a number of strains producing white colonies, and is considered as belonging to *M. varians.* Strain M 849 showed negative activity in esculin degradation but very weak degradation activity was sometimes shown over a long period culturing.

Consequently, the strain according to the present invention differs in these characteristics from the description on the neotype strain of *M. varians* presented by M. Kocur and T. Martinec. But strain M 849 may be determined to be *Micrococcus varians* because the morphological, cultural and physiological characteristics coincided with those of *M. varians* while there were differences in white colonies and esculin degradation and is deposited as *Micrococcus varians* M 849 with Fermentation Research Institute, Agency of Industrial Science and Technology under the culture number FERM-P No. 4912 and also deposited as ATCC 31606 with the American Type Culture Collection, 12301 Parklawn Drive, Rockville, Md. 20852, U.S.A.

(2) Taxonomical characteristics of strain B 645 (FERM-P No. 4913) (ATCC 31607)

(a) Morphology (i) Vegetative cells:Sphere, 1.0–1.8$\mu$ m in diameter.

(ii) Occuring in packets of cells.

(iii) Non-motile.

(iv) Spores not formed.

(v) Gram-positive.

(b) Cultural characteristics (Cultivated at 30° C. unless otherwise noted.)

(i) Nutrient agar plate

Small or dott-like, circular, dark yellow to orange-colored, smooth, glistering and opaque convex with regular edge.

(ii) Nutrient agar slant

Slow, moderate to poor growth. Orange-yellow to orange-colored and slightly raised filiform with a smooth and soft surface. Medium unchanged.

(iii) Nutrient broth

Slow-growing, turbid with small sediment. Pellicle and ring not formed. Odorless, Pigment not produced.

(iv) Nutrient gelatin stab (20° C.)

Poor growth. Liquefaction because of non-solidification by cooling after 5 day incubation at 30° C.

(v) Litmus milk

Unchanged at early stage. Coagulation after 10 days to gradual peptonization without color change of litmus.

(c) Physiological characteristics (i) Reduction of nitrates:Negative.

(ii) Gas production in nitrate broth:Negative.

(iii) MR test:Negative.

(iv) Acetoin production:Negative.

(v) Indole production-Negative.

(vi) H$_2$S production:Negative.

(vii) Starch hydrolysis ( by the same procedure as in strain M 849):Negative at pH 7.0 and positive at pH 9.5.

(viii) Citrates utilization:Negative in Simmons' media and positive in Christensen's medium.

(ix) Pigment:Water-soluble pigment not produced in a medium while colonies were yellow to orange-colored.

(x) Urease:Negative.

(xi) Oxidase (Kovac's method):Negative.

(xii) Catalase:Positive (even in 1% glucose-supplemented medium).

(xiii) Growth conditions:Optimum pH for growth was 6.0–8.5. Good growth even at pH 9.5 and 10.5. Almost no growth below pH 5.0. Optimum temperature was 25°–35° C. No growth above 40° C. or below 17° C.

(xiv) Behavior to oxygen:Aerobic.

(xv) OF test (According to the same method as in strain M 849):Aerobic growth in case of glucose and mannitol as a carbon source but no growth under anaerobic condition, which was confirmed by Evans and Kloos' method above mentioned. Acid and gas not produced under aerobic and anaerobic conditions.

(xvi) Acid production from various sugars under aerobic condition:

| | | |
|---|---|---|
| (1) | L-Arabinose | — |
| (2) | D-Xylose | — |
| (3) | D-Glucose | — |
| (4) | D-Mannose | — |
| (5) | D-Fructose | — |
| (6) | D-Galactose | — |
| (7) | Maltose | — |
| (8) | Sucrose | — |
| (9) | Lactose | — |
| (10) | Trehalose | — |
| (11) | D-Sorbitol | — |
| (12) | D-Mannitol | — |
| (13) | Inositol | — |
| (14) | Glycerine | — |
| (15) | Starch | — |

— : Not produced

No gas production from all the carbohydrates.

(xvii) Degradation of esculin:Negative.

(xviii) Degradation of hippuric acid:Negative.

(xix) Degradation of arginine:Negative.

(xx) Deamination of phenylalanine:Negative.

(xxi) Coagulase:Negative.

(xxii) Hemolysis:Negative.

(xxiii) Sodium chloride tolerance:Good growth in nutrient medium containing 5% and less NaCl. No growth in 8% and more NaCl-containing medium.

(xxiv) Phosphatase-Negative.

(xxv) Degradation of Tween 80:Negative.

(xxvi) Growth on an inorganic nitrogen agar:Almost no growth (according to the same method as that in strain M 849).

(xxvii) Liquefaction of gelatin:Positive (according to Frazier gelatin agar method).

(xxviii) Hydrolysis of casein:Positive (according to solubilization in skim milk agar).

(xxix) DNase-Negative.

From the above results, strain B 645 was identified to be one of bacteria belonging to genus Micrococcus. The taxonomical characteristics of the strain were in good agreement with those of a neotype strain of *Micrococcus luteus* described in Bergey's Mannual of Determinative Bacteriology, 8th Edition (1974) and the above-referred M. Kocur, Z. Pacova and T. Martinec's paper appeared in Intern. j. Syst. Bact. 22, 218 (1972). Therefore, strain B 645 according to the present invention was determined to be *Micrococcus luteus* and is deposited as *Micrococcus luteus* B 645 with Fermentation Research Institute, Agency of Industrial Science and Technology under the culture number FERM-P No. 4913 and also deposited as ATCC 31607 with the American Type Culture Collection, 12301 Parklawn Drive, Rockville, Md. 20852, U.S.A.

CULTIVATION OF THE MICROORGANISM

Production of the enzyme according to the present invention is accomplished by cultivating the microorganisms according to the present invention by aerobic shaking culture or submerged culture which is known per se. A medium used for this purpose is known one, namely, which contains 4–10% of carbohydrate as a carbon source, such as starch from corn, potato or sweet potato, soluble starch, dextrin, acid-treated starch, amylose and amylopectin, and appropriate amount of nitrogen source such as, soy bean meal, dried yeast, milk casein, peptone, meat extracts, corn steep liquer, yeast extract, peptides-containing material and amino acids or a mixture thereof. Furthermore, a small amount of inorganic salts, for example, $K_2HPO_4$ and $MgSO_4.7H_2O$ is added. The enzyme according to the present invention can be produced and accumulated by cultivating the microorganisms according to the present invention aerobically in said medium, pH 7–10.5, at 25°–40° C., preferably 30°–37° C., for 24–96 hours.

RECOVERY OF THE ENZYME

The enzyme according to the present invention may be recovered and purified by the known process which has been employed for recovery and purification of enzymes from various cultured materials. For example, the following methods may be employed independently or in their combination:Concentration of a cultured broth filtrate by evaporation under reduced pressure or ultrafiltration, salting-out with ammonium sulfate, sodium sulfate or sodium chloride, fractional precipitation with organic solvent such as methanol, ethanol and acetone, adsorption and elution process with an appropriate adsorbant such as starch, DEAE cellulose and cross-linked dextran, precipitation with protein-precipitation agent, isoelectric precipitation or electric dialysis.

ASSAY OF THE ENZYME ACTIVITY

Various methods for assay of cyclodextrin glycosyotransferase activity have been reported. It has been found that there is a correlationship between the two activity values obtained by sugar-transfer method by H. Bender (Arch. Microbiol. 11, 271–282 (1977) and modified cyclodextrin production method with glucoamylase by M. Matzuzawa et al (Die Stärke 27, 410–413 (1975) ), respectively. Therefore, the sugar-transfer method is mainly employed.

SUGAR-TRANSFER METHOD BY H. BENDER

A mixture containing 0.50% cycloheptaamylose and 0.025% maltotriose in 0.05 M phosphate buffer solution (pH 7.0) is prepared. To 1.9 ml of the mixture is added 0.1 ml of enzyme solution and the mixture is incubated at 37° C. for 30 min. The reaction is stopped by heating with boiling water for 10 min. A 0.5 ml portion of the reaction mixture is poured into 0.8 ml of 0.2 M phosphate buffer solution (pH 6.0) containing 40 units of β-amylase. The mixture is incubated at 37° C. for 30 min., and then reducing activity of the mixture is measured by Somogi-Nelson's method. The same procedure is repeated as a control except that water is used in place of the enzyme solution. The reducing activity corrected with the control value is converted to amount of glucose, which is defined as sugar-transfer activity. One unit of the activity is defined as an amount of enzyme required for production of 1 mg of glucose calculated from the reducing activity at 37° C. for 1 min.

METHOD USING GLUCAMYLASE

A mixture of 1.0 ml of 1.0% soluble starch solution in 0.1 M Veronal buffer solution, pH 8.0, containing 1 mM $CaCl_2$ as a substrate, and 0.1 ml of an appropriately diluted enzyme solution, is incubated at 50° C. for 2 hours. After pH is adjusted to 6.0 and the volume of the reaction mixture is filled up to 2.0 ml with water, the mixture is heated at 100° C. for 10 min. Then, 100μ g of glucamylase is added and the mixture is incubated at 40° C. for 1 hour to hydrolyze starch and oligasaccharide. Glucose thus produced is quantitatively determined by Somogi-Nelson's method. The same procedure is carried out using water in place of enzyme solution as a control. An amount of cyclodextrins produced is calculated from a difference between the above-mentioned two values.

Purification and physico-chemical properties of the enzyme are shown with Micrococcus varians M 849, as there is almost no difference in the properties of enzyme between Micrococcus luteus P. 645 and M. varians M 849.

PURIFICATION OF THE ENZYME

A cultured medium of Micrococcus varians M 849 is centrifuged to remove cells. Acetone is added to the supernatant to precipitate the enzyme. The precipitate is dissolved in water. The solution is subjected to fractional precipitation by ammonium sulfate salting out. The precipitate obtained between 45 and 65% saturation of ammonium sulfate is purified by column chromatography with DEAE Sephadex A-50 and then by gel filtration with Sephandex G-100. The purified enzyme thus obtained give a single band detected with coumassie brilliant blue in disc electrophoresis with polyacrylamide gel at pH 8.3. This band also shows the enzyme activity. Table 1 shows a typical result of the purification.

TABLE 1

| Process | Volume (ml) | Activity (U/ml) | Total activity (U) | Specific activity (U/mg of protein) | Recovery (%) |
|---|---|---|---|---|---|
| Cultured medium filtrate | 1800 | 8.6 | $1.55 \times 10^4$ | 1.8 | 100 |
| Acetone precipitate dissolved in water | 1240 | 9.5 | $1.18 \times 10^4$ | 2.1 | 76 |
| Ammonium sulfate saturated fraction | 30 | 284.0 | $0.85 \times 10^4$ | 14.0 | 55 |
| DEAE-Sephadex eluate | 680 | 6.8 | $0.46 \times 10^4$ | 25.6 | 30 |
| Sephadex G-100 Fraction | 190 | 18.0 | $0.34 \times 10^4$ | 43.4 | 22 |

(1) Enzyme action and substrate specificity

The enzyme according to the present invention acts on various kinds of starch, for example, potato, starch, corn starch and dextrin to make their reactivity to iodine negative and produce a large amount of cyclodextrins without showing substantial increase of reducing activity. In addition to the cyclodextrins, maltotetraose, maltotriose, maltose and glucose are produced as the final reaction products. The same final reaction products are also obtained by treating oligosaccharides having α-1,4-glycoside bonds with the enzyme. Therefore, the enzyme of the present invention can be defined to be cyclodextrin glycosyltransferase (E.C. 2.4.1.19).

However, the cyclodextrin glycosyltransferase according to the present invention is capable of producing α-cyclodextrin as a main reaction product by regulating pH, substrate concentration and enzyme concentration although the enzyme usually produces β-cyclodextrin dominantly, while conventional cyclodextrin glycosyltransferases produce only one type of cyclodextrin as a main product.

(2) Optimum pH and pH stability

Acetate buffer solution (pH 4.0–6.0), Veronal buffer solution (pH 6–8.5) and glycine-sodium hydroxide buffer solution (pH 8.5–12.0) were used for studies on the action and stability of the enzyme at 37° C.

Figure 1:
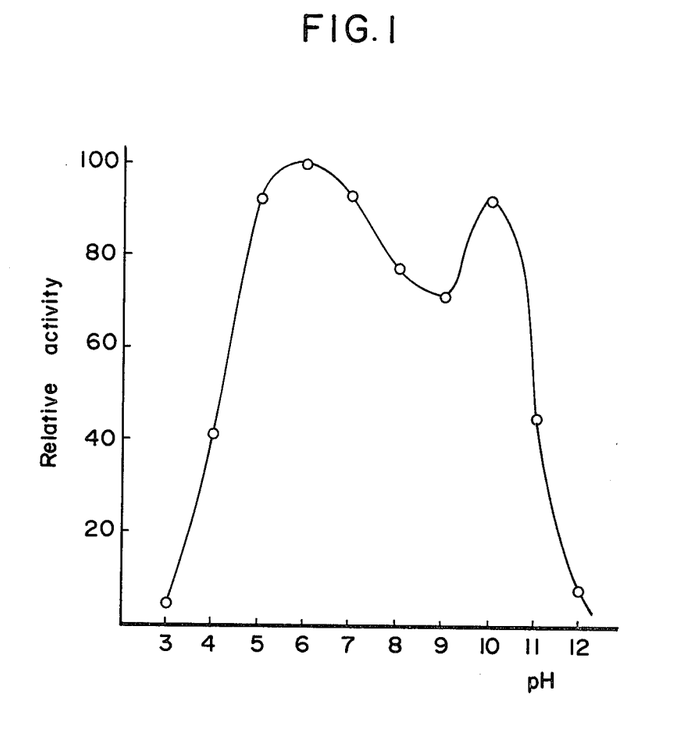
FIG. 1 shows the effect of pH at 37° C. on the activity of the enzyme according to the present invention.
Figure 2:
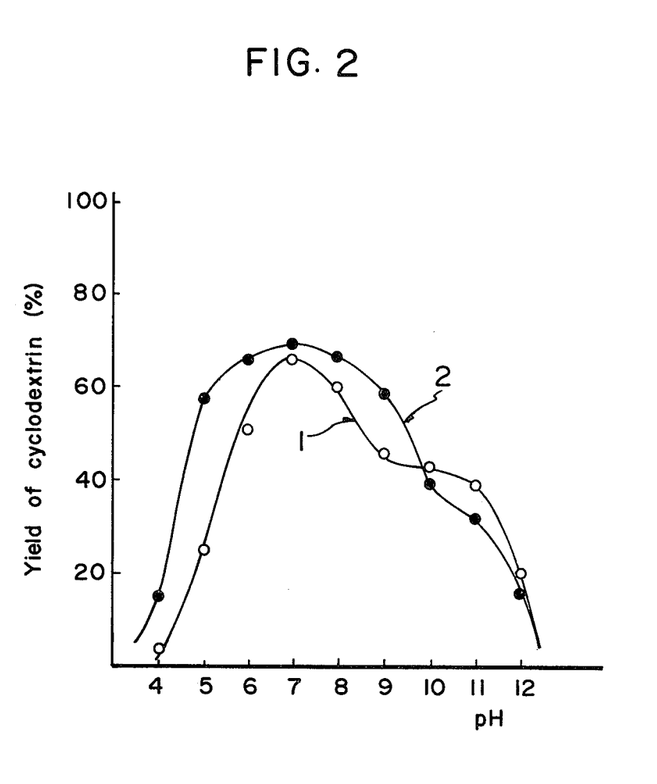
FIG. 2 shows the effect of pH at 37° C. on the yields of cyclodextrins by the enzyme (1 ... strain M 849, 2 ... strain B 645).

FIGS. 1 and 2 shows the optimum pH for the activity and the yield of cyclodextrins of the enzyme, respectively. In FIG. 1, the axis of ordinate represents relative activity in % of sugar-transfer activity measured by Bender's method and the axis of abscissa represents pH. In FIG. 2, the axis of ordinate represents recovery in % of cyclodextrin production from starch measured by glucamylase method and the axis of abscissa represents pH, where the open circles (curve 1) and closed circles (curve 2) show the enzymes from *Micrococcus varians* M 849 and *Micrococcus luteus* B 645, respectively. The enzyme according to the present invention shows high activity in considerably wide range of pH, between 4.5 and 10.5 and the optimum pH is between 5 and 8. There is also another activity peak around pH 10.

Figure 3:
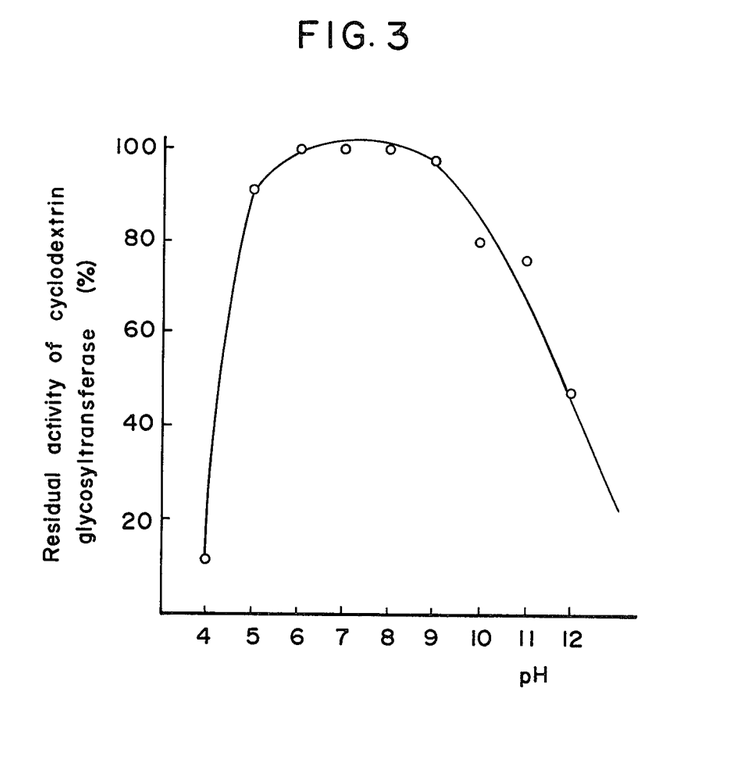
FIG. 3 shows the effect of pH on the stability of the enzyme at 37° C.

FIG. 3 shows the pH stability at 37° C. of the enzyme in which measurement of residual activity after treatment of the enzyme at various pH for 24 hours at 37° C. show almost no inactivation between pH 5 and pH 9 as shown in FIG. 3.

(3) Effect of temperature

Figure 4:
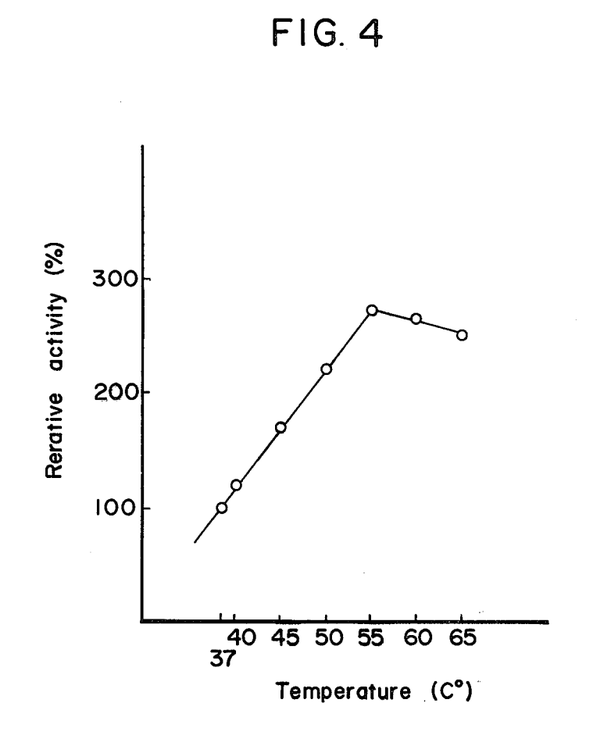
FIG. 4 shows the effect of temperature at pH 7 on the activity of the enzyme produced by strain M 849.

FIG. 4 shows the enzyme activity measured at various temperatures and pH 7, where the axis of ordinate represents the relative activity (calculated the value at 37° C. as 100) and the axis of absissa represents temperature in centigrade. As shown in this figure, the activity increases with a raise of temperature up to 40°–55° C. The optimum temperature is 55°–65° C.

(4) Inactivation of the enzyme by pH and temperature

Figure 5:
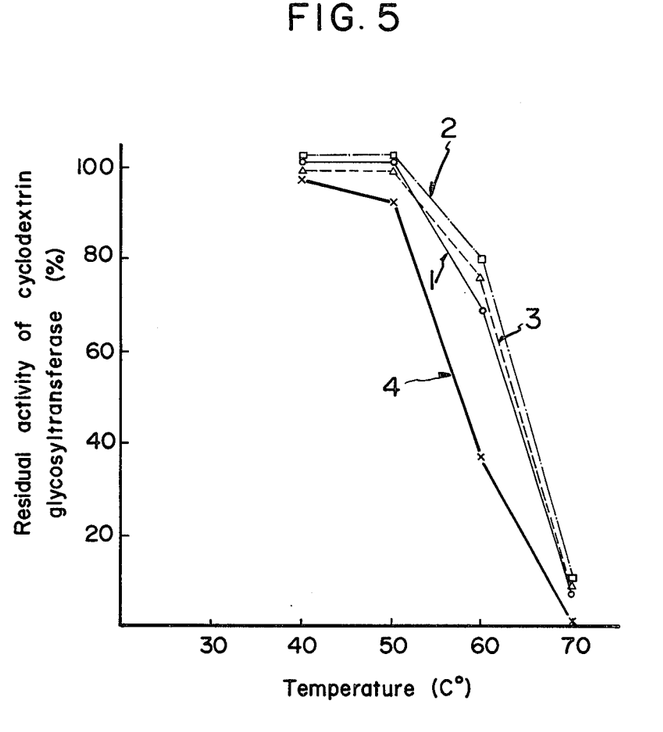
FIG. 5 shows the residual activity measured after treatment of the enzyme solution at various pH and temperatures.

FIG. 5 shows the residual activity measured after treatment of the enzyme solution (containing 5 mM Ca) at pH 5.0, 7.0, 9.0 and 11.0 for 15 min, where the axis of ordinate represents the residual activity in % and the axis of abscissa represents temperature in centigrade and also curves 1, 2, 3 and 4 represent the results obtained at pH 5.0, 7.0, 9.0 and 11.0, respectively. No inactivation is shown between pH 5 and pH 9 below 50° C. and only 20–30% of the activity is lost at 60° C.

(5) Inhibition, activation and stabilization

Figure 6:
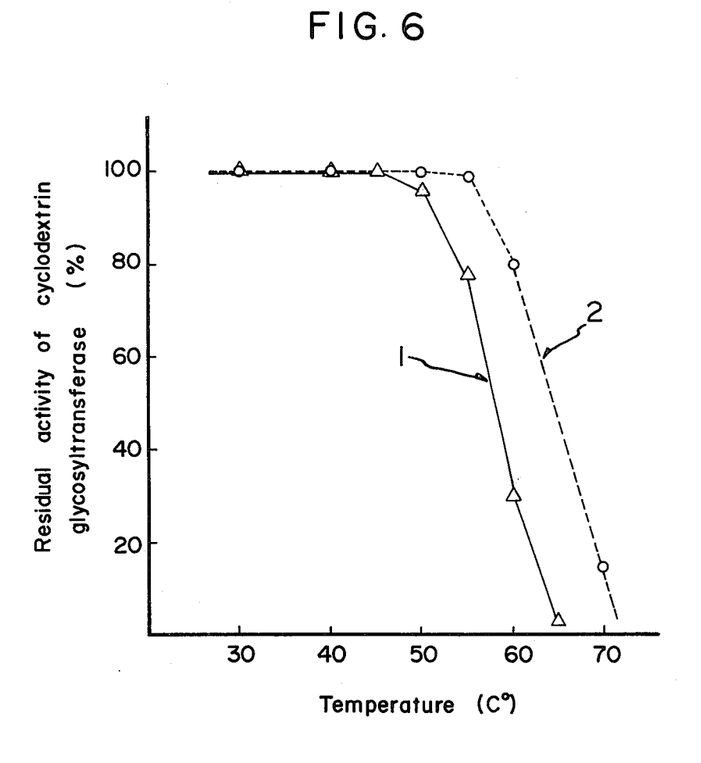
FIG. 6 shows the residual activity in % after treatment at various temperatures for 15 min. in absence and in presence of $10^{-2}$ M calcium chloride.

Tab, 2 shows the residual activity after treatment of the purified enzyme with various inhibitors or inorganic salts in 0.05 M phosphate buffer solution (pH 7) at 37° C. for 1 hour. The enzyme of the present invention is inhibited by metal ions such as copper, iron and mercury and ethylendiamine tetraacetic acid. The thermostability of the enzyme is enhanced by addition of $10^{-2}$ M–$10^{-3}$ M calcium chloride. The present enzyme is stable in presence of $Ca^{++}$ even at almost 5° C. higher than the temperature at which the enzyme is inactivated in absence of the metal ion, as shown in FIG. 6, wherein the axis of ordinate represents the residual activity in % after treatment at various temperatures for 15 min. and the axis of abscissa represents temperature in centigrade and also the solid line (1) and interrupted line (2) represent the results in absence and in presence of $10^{-2}$ M calcium chloride, respectively.

TABLE 2

| Additives | Concentration (mM) | Residual activity (%) |
| --- | --- | --- |
| CaCl$_2$ | 1.0 | 100 |
| MgCl$_2$ | 1.0 | 100 |
| ZnCl$_2$ | 1.0 | 100 |
| MgSO$_4$ | 1.0 | 100 |
| FeSO$_4$ | 0.5 | 10 |
| CuSO$_4$ | 0.5 | 6 |
| CoCl$_2$ | 0.5 | 88 |
| HgCl$_2$ | 0.5 | 5 |
| Ethylenediaminetetraacetic acid | 1.0 | 2 |
| p-Chloromercuribenzoic acid | 1.0 | 95 |
| Diisopropylfluorophosphate | 1.0 | 100 |
| Monoiodoacetic acid | 1.0 | 97 |
| O-Phenanthroline | 1.0 | 100 |

(6) Molecular weight etc.

(i) The purified enzyme preparation provided a single symmetrical peak in ultracentrifugation pattern. Sedimentation constant, $S_{20, w}$, was $5.40$–$5.60 \times 10^{-13}$ which was calculated from the experimental results obtained with 0.5, 0.3 and 0.2% protein concentration. Diffusion constant, $D_{(w)}$, was $5.84 \times 10^{-7}$ measured with an interfacial cell. Therefore, the enzyme of the present invention has a molecular weight of 85,000±2,000.

(ii) The purified enzyme preparation gave a single band in electrofocusing with Ampholine and sucrose gradient between pH 3 and pH 10 at 700 V and 3 mA for 48 hours in a LKB 810 electrofocusing column. The isoelectric point has been found to be pH 4.2.

(iii) Tab. 3 shows amino acid composition of the enzyme.

TABLE 3

| Amino acid | Amount of amino acid (g) per enzyme protein (100g) | Number of amino acid residue per enzyme molecule |
| --- | --- | --- |
| Lysine | 2.5 | 13.7 |
| Histidine | 2.7 | 13.4 |
| Arginine | 4.7 | 18.9 |
| Aspartic | 17.0 | 101.4 |
| Threonine | 7.0 | 48.4 |
| Serine | 6.7 | 53.3 |
| Glutamic | 9.4 | 50.3 |
| Proline | 3.4 | 23.9 |
| Glycine | 6.2 | 74.0 |
| Alanine | 3.1 | 30.4 |
| Valine | 6.2 | 42.7 |
| Methionine | 0.8 | 4.3 |
| Isoleucine | 6.9 | 41.6 |
| Leucine | 5.3 | 32.5 |
| Tyrosine | 7.3 | 30.9 |
| Phenylalanine | 4.8 | 22.3 |
| Tryptophan | 3.6 | 13.3 |
| Half-cystine | 0.7 | 4.7 |
| NH$_3$ | 1.7 | 70.7 |
| Total | 100 | |

(7) Crystal structure

The purified enzyme crystallizes in ammonium sulfate solution. The crystal has dodecahedron structure of which specific activity is 45 U/mg of protein.

PRODUCTION OF THE CYCLODEXTRINS

The substrate, for example, starchs such as potato starch, corn starch or soluble starch and degraded starch such as dextrin, is dissolved in water with heating. To the solution is added an enzyme preparation obtained from various steps of purification, such as a cultured medium of the microorganism of the present invention capable of producing the enzyme, cultured medium filtrate, concentrate thereof, or purified enzyme, after the pH is adjusted to 4.5–10.5, preferably 6–7 for the production of total cyclodextrin. After incubation at a temperature of 40°–65° C. for an appropriate time, the reaction product is precipitated by one of the known methods. The precipitate is collected and washed with water. Recrystallization by the known method of the washed precipitate provides crystalline cyclodextrins.

The cyclodextrins thus obtained can be fractionated into α-, β- and γ-cyclodextrin according to a method described by D. French et al (J. Am. Chem. Soc. 71, 353 (1949), each of which may be obtained as a white crystalline purified preparation. In the physico-chemical properties of each preparation, crystal form, melting point, specific optical rotation, iodo-starch reaction, reducing sugar content and infrared spectrum were confirmed to coincide with those of authentic α-, β- or γ-cyclodextrin.

Relationship betweein cyclodextrin productions and the condition for producing thereof

EXPERIMENT 1

A solution of 10 g of soluble starch dissolved in 100 ml of water containing 0.05% $CaCl_2.2H_2O$ was prepared with heating. After the pH was adjusted to 6.0, various amounts of enzyme and 5 ml of trichloroethylene were added. The mixture was incubated at 50° C. or 60° C. for 2 days. Cyclodextrins were recovered as precipitation of its trichloroethylene complex. Table 4 shows the results.

TABLE 4

| Enzyme | Amount of enzyme used (U/g of starch) | Cyclodextrin production (%) (Recovery from starch | |
|---|---|---|---|
| | | 50° C. | 60° C. |
| Cultured medium filtrate of strain M 849 | 1 | 50 | 52 |
| | 2 | 55 | 60 |
| | 3 | 58 | 55 |
| | 5 | 52 | 45 |
| | 10 | 48 | 40 |
| Purified preparation | 1 | 50 | 51 |
| | 2 | 58 | 62 |
| | 3 | 56 | 54 |
| | 5 | 50 | 43 |
| | 10 | 47 | 38 |

Cyclodextrins were produced in 50–52% yield by using one unit of enzyme per gram of starch and in higher yield such as 60% by using 2 units per gram of starch in the case of the enzyme of the present invention and further there shows a tendency of rather decrease of the total cyclodextrins yield with using more enzyme than this optimal units.

EXPERIMENT 2

Soluble starch was dissolved with heating in water containing 0.05% $CaCl_2.2H_2O$. The solution was diluted to various concentration indicated in Table 5. To the solutions, were added various amounts of the enzyme of the present invention after the pHs being adjusted to various values, as indicated in Table 5. The reaction mixtures were incubated at 50° C. for 2 days, and then the amounts of α-, β- and γ-cyclodextrins, respectively were determined by thin layer chromatography. Table 5 shows the results.

TABLE 5

| Concentration of starch (W/V %) | Amount of enzyme (U/g of starch) | pH | Cyclodextrins production (%) (Recovery from starch) | | |
|---|---|---|---|---|---|
| | | | α-cyclo-dextrin | β-cyclo-dextrin | γ-cyclo-dextrin |
| 1 | 10 | 5 | 40 | 19 | 0 |
| 1 | 10 | 6 | 36 | 31 | 0 |
| 1 | 10 | 7 | 19 | 43 | 3 |
| 1 | 10 | 8 | 0 | 55 | 5 |
| 1 | 10 | 10 | 0 | 55 | 10 |
| 1 | 1 | 5 | 6 | 49 | 3 |
| 1 | 5 | 5 | 22 | 40 | 0 |
| 1 | 8 | 5 | 29 | 36 | 0 |
| 1 | 10 | 5 | 40 | 19 | 0 |
| 1 | 15 | 5 | 42 | 15 | 0 |
| 2 | 10 | 5 | 36 | 32 | 0 |
| 3 | 10 | 5 | 20 | 44 | 0 |
| 5 | 10 | 5 | 12 | 45 | 5 |
| 10 | 10 | 5 | 6 | 45 | 9 |
| 1 | 10 | 6 | 36 | 32 | 0 |
| 2 | 10 | 6 | 33 | 30 | 0 |
| 3 | 10 | 6 | 12 | 48 | 0 |
| 5 | 10 | 6 | 5 | 50 | 3 |
| 10 | 10 | 6 | 4 | 46 | 5 |

When treating starch with the enzyme of the present invention, a ratio of α-, β- and γ-cyclodextrins in the reaction product depends upon the substrate concentration, amount of enzyme used and pH of the reaction mixture among various reaction conditions. For example, under the conditions that the substrate concentration is less than 2% at pH 4.5–6.5 with 10 U/g of starch, α-cyclodextrin production is larger than β-cyclodextrin. But, at pH 7–10, dominant reaction product is β-cyclodextrin without dependency on substrate concentration and enzyme amount used. In both cases γ-cyclodextrin production is very small. Namely, it has been found that α-cyclodextrin is in larger amount than β-cyclodextrin under the reaction condition in which the pH of the reaction mixture is 4.5–6.5 at a substrate concentration of less than 2% (W/V) with enzyme at a concentration of 10 U/g of starch substrate. It has also been found that this property of the enzyme is common to conventional β-cyclodextrin glycosyltransferase which has been known to produce mainly β-cyclodextrin.

The following examples illustrate the present invention more in detail.

EXAMPLE 1

A 60 ml portion of liquid medium consisting of 4.0% soluble starch. 1.0% soy bean meal, 0.3% yeast extract, 0.3% disodium glutamate, 0.2% $K_2HPO_4$, 0.05% $MgSO_4.7H_2O$ and 0.03% $CaCl_2.2H_2O$ (pH 8.0) was dispensed to 500 ml-Sakaguchi flasks and sterilized by autoclaving. The medium was inoculated with a loop of *Micrococcus varians* M 849, FERM-P No. 4912 slant culture and incubated with shaking at 32° C. for 3 days.

One liter of the cultured medium was centrifuged to remove cells. To the supernatant was added $CaCl_2.2H_2O$ at a final concentration of 0.1%. The mixture was cooled. The enzyme was precipitated by adding 2.5 volumes of cold acetone. The precipitate was collected by centrifugation and dried under reduced pressure to provide 9.5 g of crude enzyme powder.

A solution of 300 g of soluble starch dissolved in 3 l of water (containing 6 g of $CaCl_2.2H_2O$) with heating was prepared. After the pH of the solution was adjusted to 6.0 with HCl, 1 g (770 U) of the crude enzyme powder mentioned above was added. The mixture was incubated at 60° C. for 48 hours and then cooled with water. To the cooled reaction mixture was added 200 ml of toluene with thoroughly stirring and mixing to precipitate the reaction product. The precipitate thus formed was collected by filtration and washed with water, and then suspended in 1 liter of water. Toluene was evaporated by heating the suspension. To the solution thus obtained was added 4 g of active carbon. The mixture was filtered at higher than 60° C. Cooling the filtrate gave 180 g of cyclodextrins (60% of yield based on starch) as white crystals.

EXAMPLE 2

The same procedure described as in Example 1 was repeated except using 100 ml (860 U) of a supernatant of the cultured medium collected by centrifugation, obtained by cultivation carried out in the same manner as in Example 1, in place of 1 g of the crude enzyme preparation. Treatment of soluble starch provided 150 g of the cyclodextrins (50% of yield) as white crystals.

EXAMPLE 3

The same procedure as described in Example 1 was repeated except using *Micrococcus luteus* B 645, FERM-P No. 4913 according to the present invention in place of *M. varians* M 849. Treatment of soluble starch with 1.0 g (650 U) of the crude enzyme preparation provided 160 g of the cyclodextrins (53% of yield) as white crystals.

EXAMPLE 4

A solution of 300 g of soluble starch dissolved in 3 l of water (containing 6 g of $CaCl_2.2H_2O$) was prepared with heating. After the pH of the solution was adjusted to 6.0 with dilute hydrochloric acid, 1.5 g (1155 U) of the crude enzyme preparation obtained in Example 1 was added. The mixture was incubated at 50° C. for 72 hours. Then the reaction mixture was concentrated under reduced pressure to 1 liter, which was cooled to give crystals. The crystals thus produced were collected by filtration and dissolved in 0.7 l of water with heating. To the solution was added 3 g of active carbon and the mixture was filtered at higher than 60° C. Cooling the filtrate provided 100 g of cyclodextrins (33% of yield) as white crystals.

EXAMPLE 5

A solution of 300 g of soluble starch dissolved in 3 l of water (containing 6 g of $CaCl_2.2H_2O$) was prepared with heating. After the pH of the solution was adjusted to 6.0 with dilute hydrochloric acid. 0.5 g (335 U) of the crude enzyme preparation obtained in Example 1 and 200 ml of trichloroethylene were added. The mixture was incubated at 50° C. for 48 hours. Then the reaction product was precipitated by cooling with stirring. The precipitate thus obtained was collected and washed with water, and then suspended in 1 liter of water. The suspension was heated to remove trichloroethylene by evaporation. To the solution thus obtained was added 4 g of active carbon and the mixture was filtered at higher than 60° C. The filtrate was cooled to which an equal volume of isopropanol was added. The mixture was allowed to stand overnight to give 190 g of cyclodextrins (63% of yield) as white crystals. The ratio of $\alpha$-, $\beta$- and $\gamma$-cyclodextrin of the crystalline products was $\alpha:\beta:\gamma = 5:85:10$.

EXAMPLE 6

A solution of 100 g of soluble starch dissolved in 10 l of water (containing 10 g of $CaCl_2.2H_2O$) with heating was prepared. After the pH of the solution was adjusted to 5.0 with HCl, 1.5 g (1155 U) of the crude enzyme powder obtained in Example 1 was added. The mixture was incubated at 50° C. for 48 hours and then cooled with water. To the cooled reaction mixture was added 300 ml of toluene with thoroughly stirring and mixing. A precipitate was formed. The mixture was filtered to collect the precipitate and filtrate separately. The precipitate was suspended in 60 ml of water. Toluene was evaporated by heating. To the solution thus obtained was added 0.3 g of active carbon. The mixture was filtered at higher than 60° C. Cooling the filtrate provided 15 g of $\beta$-cyclodextrin (15% of yield based on starch) as white crystals.

The filtrate obtained by adding toluene to the reaction mixture mentioned above was concentrated by evaporation under reduced pressure up to 1 liter and cooled. To the concentrate was added 30 ml of tetrachloroethane with thoroughly stirring and mixing to precipitate the reaction product. The precipitate thus produced was collected by filtration, washed with water and suspended in 100 ml of water. After tetrachloroethane was removed by heating, 0.5 g of active carbon was added to the solution. The mixture was filtered at higher than 50° C. The filtrate was cooled. An equal volume of isopropanol was added to the cooled filtrate. The mixture was allowed to stand overnight to give 25 g of $\alpha$-cyclodextrin (25% of yield based on starch) as white crystals.

Two kinds of cyclodextrins obtained separately as described above were identified to be $\alpha$- and $\beta$-cyclodextrins, respectively, based on their melting points and by specific optical rotation, iodo-starch reaction and thin layer chromatography.

EXAMPLE 7

A solution of 300 g of soluble starch dissolved in 3 l of water (containing 6 g of $CaCl_2.2H_2O$) was prepared with heating. After the pH of the solution was adjusted to 10 with $Na_2CO_3$, 0.5 g (325 U) of crude enzyme preparation obtained in Example 3 and 200 ml of toluene were added. The reaction mixture was incubated at 55° C. for 48 hours. The reaction product was precipitated by cooling the mixture with stirring. The precipitate was washed with water and suspended in 1 liter of water. The suspension was heated to remove toluene by evaporation. To the solution thus obtained was added 4 g of active carbon. The mixture was filtered at higher than 60° C. To the filtrate was added an equal volume of isopropanol after cooling. The mixture was allowed to stand overnight to provide 180 g (60% of yield) of cyclodextrins as white crystals.

The ratio of $\alpha$-, $\beta$- and $\gamma$-cyclodextrins of the crystal was analyzed to be $\alpha:\beta:\gamma = 0:95:5$.

EXAMPLE 8

The same procedure as described in Example 6 was repeated except using 2.0 g (1300 U) of the crude enzyme preparation obtained in Example 3 in place of 1.5 g of the crude enzyme of Example 6. Treatment of soluble starch provided 30 g of α-cyclodextrin (30% of yield based on starch) and 12 g of 62-cyclodextrin (12% of yield).

EXAMPLE 9

A solution of 300 g of potato starch dissolved in 3 l of water (containing 6 g of $CaCl_2.2H_2O$) was prepared with heating. The pH of the solution was adjusted to 6.0 and then 0.06 g of α-amylase (Neospitase K) was added. The mixture was incubated at 80° C. for 10 min., and then heated at 100° C. for 10 min. After cooling, 1 g (770 U) of crude enzyme preparation obtained in Example 1 was added. The mixture was incubated at 60° C. for 48 hours and cooled with cold water. To the mixture was added 200 ml of toluene with thoroughly stirring and mixing to precipitate the reaction product. The precipitate was collected by filtration and washed with water, and then suspended in 1 liter of water. The suspension was heated to remove toluene by evaporation. To the solution thus obtained was added 4 g of active carbon. The mixture was filtered at higher than 60° C. Cooling of the filtrate provided 170 g of cyclodextrins (57% yield based on starch) as white crystals.

What is claimed is:

1. A process for producing cyclodextrins which comprises reacting starch or degraded starch as a substrate with a cyclodextrin glycosyltransferase enzyme preparation selected from the group consisting of cultured medium, cultured medium filtrate, concentrate thereof or enzyme preparation which is obtained by cultivating microorganisms belonging to genus Micrococcus capable of producing cyclodextrin glycosyltransferase, to provide cyclodextrins at a pH and a temperature effective for said reaction.

2. A process as claimed in claim 1 wherein α-cyclodextrin is mainly produced by the use of a concentration of a starchy material as a substrate of less than 2% (W/V), a concentration of enzyme activity of cyclodextrin glycosyltransferase more than 10 U per g of the substrate, and pH of the reaction mixture between 4.5 and 6.5.

3. A process as claimed in claim 1 wherein β-cyclodextrin is mainly produced by the use of a pH of the reaction mixture between 7 and 10.

4. A process as claimed in claim 1 wherein said enzyme preparation is of various degrees of purification.

5. A process as claimed in claim 1 wherein a purified enzyme preparation is used.

6. A process for producing cyclodextrin glycosyltransferase which comprises cultivating aerobically a microorganism belonging to genus Micrococcus capable of producing cyclodextrin glycosyltransferase in a nutrient medium under the condition of pH 7–10.5, at the temperature of 25°–40° C. for 24–96 hours, and effecting purification of the product of the cultivation step by the use of a procedure selected from the group consisting of concentration of the cultured medium, salting out, fractional precipitation, adsorption, elution, precipitation, isoelectric precipitation, electric dialysis independently and a combination thereof.

7. A process as claimed in claim 6 wherein said microorganism is selected from the group consisting of *Micrococcus varians* M 849 (FERM P-4912, ATCC 31606) and *Micrococcus luteus* B 645 (FERM P-4913, ATCC 31607).

8. A process as claimed in claim 6 wherein said temperature is 30°–37° C.

* * * * *